United States Patent [19]

Ward

[11] 4,278,685
[45] Jul. 14, 1981

[54] AMIDE DERIVATIVES

[75] Inventor: Terence J. Ward, Slough, England

[73] Assignee: John Wyeth & Brother Limited, Maidenhead, England

[21] Appl. No.: 958,762

[22] Filed: Nov. 8, 1978

[30] Foreign Application Priority Data

Nov. 24, 1977 [GB] United Kingdom ............... 48921/77

[51] Int. Cl.³ .................... C07D 207/34; A61K 31/40
[52] U.S. Cl. .............................. 424/274; 260/326.43; 260/326.62
[58] Field of Search .................... 260/326.43; 424/274

[56] References Cited

U.S. PATENT DOCUMENTS

| 4,021,566 | 5/1977 | Bell | 424/274 |
| 4,118,396 | 10/1978 | Pifferi | 260/326.43 |
| 4,140,793 | 2/1979 | Ward | 260/326.43 |

OTHER PUBLICATIONS

Bell, M., J. Med. Chem. 1977, 20(4), 537–540–Chem. Abstr., 86:114984e.

Burger, A., "Medicinal Chemistry", 2nd ed., Interscience Publishers Inc., N.Y., 1960, p. 43.

Primary Examiner—Mary C. Lee
Attorney, Agent, or Firm—Arthur E. Wilfond

[57] ABSTRACT

Novel amides of formula

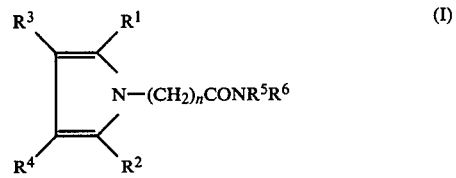

wherein $R^1$ and $R^2$ are each halogen, $R^3$ and $R^4$ are each hydrogen or lower alkyl, $R^5$ and $R^6$ are each hydrogen or lower alkyl and n is an integer of from 1 to 3 inclusive, are anti-ulcer agents which possess anti-secretory activity.

7 Claims, No Drawings

AMIDE DERIVATIVES

This invention relates to novel amide derivatives, to processes for their preparation and to pharmaceutical compositions containing them.

The novel compounds of the present invention are amides of the general formula

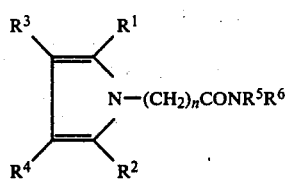

wherein $R^1$ and $R_2$ are each the proviso that at least one of $R^1$ and $R^2$ is $R_5$ and $R_6$ are each hydrogen or lower alkyl, and n is an integer of from 1 to 3 inclusive.

The term "lower" as used herein means that the radical referred to contains from 1 to 6 carbon atoms. Preferably the radical contains from 1 to 4 carbon atoms.

$R^1$ and $R^2$ can be the same or different provided that at least one is halogen (e.g. fluorine, chlorine, or bromine). Preferably both $R^1$ and $R^2$ are chlorine.

$R^3$ and $R^4$ can be the same or different. Examples of lower alkyl groups for $R^3$ and $R^4$ are methyl, ethyl, propyl and butyl. Preferably both $R^3$ and $R^4$ are hydrogen. When $R^3$ and $R^4$ are each hydrogen or lower alkyl the compounds of the invention are pyrrole derivatives.

$R^5$ and $R^6$ can be the same or different. Examples of lower alkyl groups for $R^5$ and $R^6$ are methyl, ethyl, propyl and butyl. Preferably both $R^5$ and $R^6$ are hydrogen.

n can be 1, 2 or 3 but preferably it is 1.

The compounds of the invention are amides and can be prepared by methods known in the art for preparing amides. For example, they may be prepared by a process in which a reactive derivative of an acid of general formula (II)

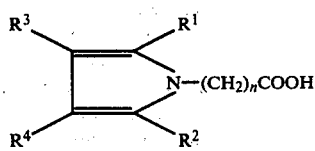

(where $R^1$, $R^2$, $R^3$ and $R^4$ have the meanings given above) is reacted with a compound of general formula (III)

 (III)

(where $R^5$ and $R^6$ are as defined above). The compound of formula (III) is ammonia or a primary or secondary amine. The reactive derivative of the acid is preferably an ester, in particular an ester of general formula (IV)

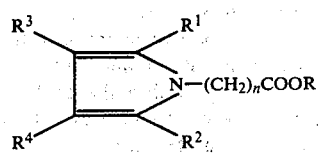

where n, $R^1$, $R^2$, $R^3$ and $R^4$ are as defined above and R is lower alkyl (e.g. methyl, ethyl, propyl or butyl).

An alternative reactive derivative of the acid of general formula (II) is an acid halide, particularly the acid chloride of general formula (V)

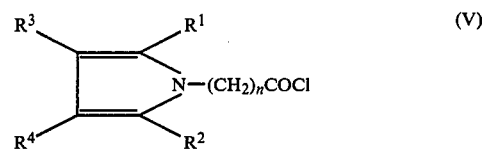

(where n, $R^1$, $R^2$, $R^3$ and $R^4$ are as defined above).

The acid of general formula (II) and its reactive derivatives (for example the ester of formula (IV) or the acid chloride of formula (V) ) may be prepared by methods known for preparing analogous compounds. For example, the compounds may be prepared by the methods described in German Offenlegunsschrift No. 2,312,006. The compounds can also be prepared by an alternative method in which a dicarbonyl compound of general formula (VI)

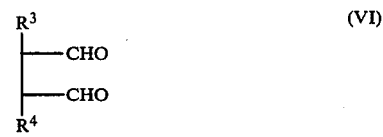

(where $R^3$ and $R^4$ are as defined above) or a functional derivative thereof, particularly a 2,5-dialkoxytetrahydrofuran of general formula (VII)

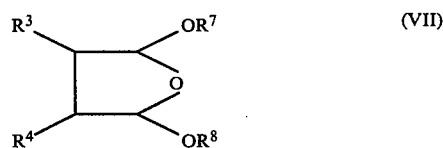

(where $R^3$ and $R^4$ are as defined above and $R^7$ and $R^8$ are each lower alkyl, preferably ethyl), is reacted with an ester of an amino acid of formula $NH_2(CH_2)_nCOOH$ to give an ester of the acid of general formula (VIII)

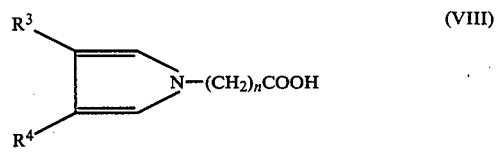

which may be halogenated, e.g. with sulphuryl chloride, to give an ester of the acid of formula (II), for example the ester of formula (IV). By suitable choice of, and proportions of reactants it is possible to halogenate the ester of the acid of formula (VIII) in the 2 and/or 5-position of the pyrrole ring. Once an ester of the acid of formula (II) has been prepared this may be converted into other reactive derivatives of the acid by standard procedures. For example, the ester may be hydrolysed to the free acid which may be reacted with, for example, thionyl chloride to give the acid chloride of general formula (V).

An alternative method of preparing the compounds of the present invention in which $R^5$ and $R^6$ are both hydrogen comprises hydrolysing a nitrile of formula (IX)

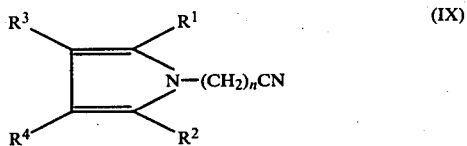

(where $R^1$, $R^2$, $R^3$, $R^4$ and n are as defined above). A preferred method of preparing the nitrile of formula (IX) comprises reacting the dicarbonyl compound of general formula (VI) or a functional derivative thereof, particularly the 2,5-dialkoxytetrahydrofuran of general formula (VII), with an aminonitrile of formula (X)

(where n is as defined above), to give a nitrile of formula (XI)

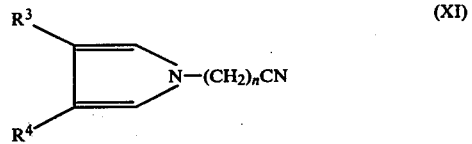

(where n, $R^3$ and $R^4$ are as defined above) which may be halogenated, eg with sulphuryl chloride, to give the nitrile of formula (IX).

Another method of preparing a compound of the invention comprises halogenating a compound of general formula (XII)

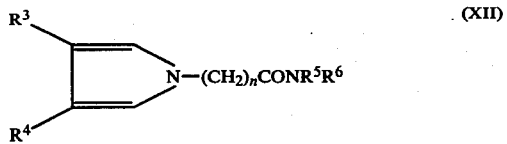

(where n, $R^3$, $R^4$, $R^5$ and $R^6$ are as defined above). The halogenation is preferably effected with sulphuryl chloride. By suitable choice of, and proportions of, reactants it is possible to halogenate the compounds of formulae (XI) and (XII) in the 2 and/or 5-positions of the pyrrole ring to give compounds in which both $R^1$ and $R^2$ are halogen or one is halogen and the other is hydrogen. The compounds of general formula (XII) can, for example, be prepared from the acid of general formula (VIII) or a reactive derivative thereof (e.g. ester) by standard procedures known for preparing amides (such as those described above for converting the reactive derivatives of the acid of formula II to its amides). Alternatively the compounds of general formula (XII) can be prepared by hydrolysing a nitrile of general formula (XI).

The compounds of the invention possess pharmacological activity. Thus the compounds are anti-ulcer agents which possess anti-secretary activity in the standard test of H. Shay, D. Sun and H. Greenstein, Gastoenterology, 1954, 26, 903-13. For example (2,5-dichloro-1H-pyrrol-1-yl)acetamide, a representative compound of the present invention shows marked activity when administered at 10 and 30 mg/kg intraduodenally. In general, the compounds, including (2,5-dichloro-1H-pyrrol-1-yl)acetamide, also possess antihypertensive activity in standard pharmacological tests.

The invention includes a pharmaceutical composition comprising a compound of general formula (I) in association with a pharmaceutically acceptable carrier. Any suitable carrier known in the art can be used to prepare the pharmaceutical compositions. In such composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredient can be dissoved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance, aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid phrmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage form can be a packaged composition the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need of the patient and the activity of the active ingredient. The invention also includes the compounds in the absence of the carrier where the compounds are in unit dosage form.

The anti-ulcer compositions of the present invention may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U.K. Patent Specification No. 1,284,394.

The following Examples illustrate the invention.

EXAMPLE 1

(2,5-Dichloro-1H-pyrrol-1-yl)acetamide

A mixture of methyl(2,5-dichloro-1H-pyrrol-1-yl)acetate (0.5 g), in ether (3 cm³), and concentrated aqueous ammonia solution (3 cm³) was stirred at room temperature overnight in a stoppered flask. The precipitated crystalline product was collected by filtration and washed with ether to give 0.07 g of title compound. The ethereal washings were dried and evaporated. The crystalline residue was triturated with diisopropyl ether to give a further 0.13 g of title compound, m.p. 183°–4° C.

EXAMPLE 2

(2,5-Dichloro-1H-pyrrol-1-yl)-N-methylacetamide

A mixture of methyl (2,5-dichloro-1H-pyrrol-1-yl)acetate (1.04 g) and methylamine (5 cm³, 33% solution in ethanol) was allowed to stand at room temperature overnight. The solvent was then evaporated and the residue crystallised from isopropanol to give the title compound (0.65 g) m.p. 193°–4° C.

EXAMPLE 3

2-(2,5-Dichloro-1H-pyrrol-1-yl)propionamide

Ethyl 2-(1H-pyrrol-1-yl)propionate (Ger. Offen. No. 2,305,632) in dichloromethane, maintained below 0° C., is treated with two equivalents of sulphuryl chloride to give ethyl 2-(2,5-dichloro-1H-pyrrol-1-yl)propionate. Treatment of this ester with ammonia in the manner of Example 1, gives 2-(2,5-dichloro-1H-pyrrol-1-yl)propionamide.

We claim:

1. An amide of the formula

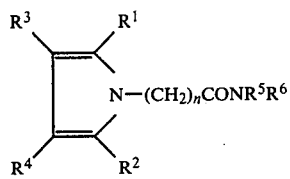

wherein $R^1$ and $R^2$ are each halogen, $R^3$ and $R^4$ are each hydrogen or lower alkyl, $R^5$ and $R^6$ are each hydrogen or lower alkyl and n is an integer of from 1 to 3 inclusive.

2. An amide as claimed in claim 1 wherein $R^1$ and $R^2$ are both chlorine.

3. An amide as claimed in claim 1 wherein $R^5$ and $R^6$ are both hydrogen.

4. An amide as claimed in claim 1 which is (2,5-dichloro-1H-pyrrol-1-yl)acetamide.

5. An amide as claimed in claim 1 which is (2,5-dichloro-1H-pyrrol-1-yl)-N-methylacetamide.

6. An amide as claimed in claim 1 which is 2-(2,5-dichloro-1H-pyrrol-1-yl)propionamide.

7. A pharmaceutical composition having antisecretory activity comprising an effective amount of an amide of the formula

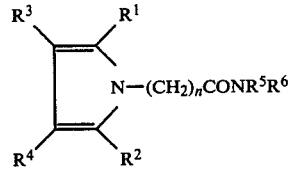

wherein $R^1$ and $R^2$ are each halogen, $R^3$ and $R^4$ are each hydrogen or lower alkyl, $R^5$ and $R^6$ are each hydrogen or lower alkyl and n is an integer of from 1 to 3 inclusive, in association with a pharmaceutically acceptable carrier.

* * * * *